United States Patent
Rigaud et al.

(10) Patent No.: US 11,596,728 B2
(45) Date of Patent: Mar. 7, 2023

(54) DEVICE AND METHOD FOR REMOVING UNDESIRABLE BIOLOGICAL AND/OR CHEMICAL ENTITIES FROM BIOLOGICAL FLUIDS

(71) Applicants: ISTITUTO SCIENTIFICO ROMAGNOLO PER LO STUDIO E LA CURA DEI TUMORI (I.R.S.T.) S.R.L, Meldola (IT); Michel Rigaud, Feytiat (FR)

(72) Inventors: Michel Rigaud, Feytiat (FR); Wainer Zoli, Meldola (IT); Francesco Fabbri, Meldola (IT); Giulia Gallerani, Meldola (IT); Pietro Fici, Meldola (IT)

(73) Assignees: Michel Rigaud, Feytiat (FR); ISTITUTO SCIENTIFICO ROMAGNOLO PER LO STUDIO E LA CURA DEI TUMORI (I.R.S.T.) S.R.L, Meldola (IT)

( * ) Notice: Subject to any disclaimer, the term of this patent is extended or adjusted under 35 U.S.C. 154(b) by 203 days.

(21) Appl. No.: 17/099,069

(22) Filed: Nov. 16, 2020

(65) Prior Publication Data
US 2021/0077707 A1    Mar. 18, 2021

Related U.S. Application Data

(62) Division of application No. 16/096,466, filed as application No. PCT/EP2017/059626 on Apr. 24, 2017, now Pat. No. 10,864,313.

(30) Foreign Application Priority Data

Apr. 26, 2016 (IT) .......................... UA2016A002865

(51) Int. Cl.
*A61M 1/36* (2006.01)
*C07K 16/30* (2006.01)

(52) U.S. Cl.
CPC .......... *A61M 1/3679* (2013.01); *C07K 16/30* (2013.01); *A61M 2202/0014* (2013.01);
(Continued)

(58) Field of Classification Search
CPC ........ A61M 1/3679; A61M 2202/0064; A61M 2202/0057; A61M 2202/0014; A61M 2206/16; A61M 2205/103; C07K 16/30
See application file for complete search history.

(56) References Cited

U.S. PATENT DOCUMENTS

| 2014/0008210 A1 | 1/2014 | Guia et al. |
| 2015/0122738 A1 | 5/2015 | Kim |
| 2015/0283318 A1 | 10/2015 | Wang et al. |

FOREIGN PATENT DOCUMENTS

| GB | 2479536 A | 10/2011 |
| WO | 2012/119646 A1 | 9/2012 |

(Continued)

OTHER PUBLICATIONS

International Search Report and Written Opinion issued in connection with the corresponding PCT/EP2017/059626, dated Jul. 5, 2017. (14 pages).

*Primary Examiner* — John Kim
(74) *Attorney, Agent, or Firm* — Lucas & Mercanti, LLP

(57) ABSTRACT

A device removing a biological and/or chemical entity (C) from extracorporeal blood (B) is disclosed. The device has a hollow capture chamber with an inlet for the entry of the extracorporeal blood (B) and an outlet for the outflow of the extracorporeal blood (B) and a capture element inside the capture chamber having a reactant surface placed in contact with the extracorporeal blood (B) and a plurality of binding agents (A) for the biological and/or chemical entity to be removed (C) such that the biological and/or chemical entity (Continued)

(C), upon exiting the capture chamber, is removed from the extracorporeal blood (B) as linked to the reactant surface.

11 Claims, 8 Drawing Sheets

(52) U.S. Cl.
CPC .............. *A61M 2202/0057* (2013.01); *A61M 2202/0064* (2013.01); *A61M 2205/103* (2013.01); *A61M 2206/16* (2013.01)

(56) References Cited

FOREIGN PATENT DOCUMENTS

| | | |
|---|---|---|
| WO | 2012/172341 A3 | 12/2012 |
| WO | 2013/023156 A1 | 2/2013 |

DEVICE AND METHOD FOR REMOVING UNDESIRABLE BIOLOGICAL AND/OR CHEMICAL ENTITIES FROM BIOLOGICAL FLUIDS

CROSS-REFERENCE TO RELATED APPLICATIONS

This application is a divisional application of U.S. patent application Ser. No. 16/096,466, filed Oct. 25, 2018, now U.S. Pat. No. 10,864,313, which is a 371 of PCT Application Ser. No. PCT/EP2017/059626, filed Apr. 24, 2017, which claims the benefit from Italian Patent Application No. UA2016A002865, filed Apr. 26, 2016, the contents of each of which are incorporated herein by reference.

TECHNICAL FIELD

The present invention relates to a device for removing at least one undesirable biological, biochemical and/or chemical entity, for example toxic substances and/or tumor cells, from a biological fluid volume, for example blood, or rather blood temporarily taken from a patient by means of an extracorporeal circuit [or extracorporeal circulation system (ECS)].

The present invention also relates to a corresponding extracorporeal circulation system comprising said device and a method for the removal of at least one undesirable biological and/or chemical entity from an extracorporeal blood volume.

In particular, the present invention relates to an "ex vivo liquid surgery device" as well as an "ex-vivo liquid surgery" system and method for the removal of circulating tumor cells (CTCs) from the total blood volume (TBV) of a cancer patient, during a repeated procedure of extracorporeal blood circulation, in order to decrease or avoid metastasis spreading and risk of relapse.

STATE OF THE ART

Circulating tumor cells (CTC) are biological entities released into the circulating bloodstream, mainly from the primary tumor, capable of giving rise to the so-called metastases (Zhank L. et al., Sci Transl Med, 2013; Baccelli I. et al., Nat Biotech, 2014; Aceto N, et al., Cell, 2014). Since metastases are the leading cause of death caused by tumors, the biological and clinical significance of these cells is unquestionable. The capture and the removal of such cells from the body of a cancer patient could limit and/or prevent the risk of metastatic spread of the disease and possible relapses, as well as a conventional surgical approach of a solid tumor can limit the disease or even cure a cancer patient.

CTCs were first identified in 1869, but only in the last 15 years an extensive scientific investigation has defined the role and the diagnostic, prognostic and predictive potential thereof. Their potential clinical value as well as their clinical value in terms of prognosis are unquestionable. In fact, detecting, "capturing" and studying these cells and the biomolecular characteristics thereof would allow for a more targeted and efficient therapeutic treatment of the patient. Subsequently, removing all, or at least a large part, of said cells, from the bloodstream would allow for a drastically reduced or avoided risk of metastatic spread of the disease, thereby increasing the survival of patients or their disease-free survival. Until now, however, the only documented clinical use of CTCs is the prognostic one defined on the basis of their abundance. Moreover, up to now, the prognostic value of the number of CTCs in the peripheral blood has been documented only in breast, colon, and prostate cancers in the metastatic stage, demonstrating a better prognosis for patients who have less than 5 CTCs/7.5 ml peripheral blood. All this is due to the intrinsic characteristics of the CTCs, i.e. their rareness, heterogeneity and plasticity.

In summary, CTCs have proved to be a valuable clinical tool only as a prognostic marker and not as a factor that can lead to a more targeted and effective therapy assisting in the choice of the drug(s) to be used in order to increase the survival of patients (Joosse S A and Pantel K, Cancer Res, 2013; Alix-Panabieres C and Pantel K, Clin Chem, 2013; Krebs M G et al., Nat Rev Clin Oncol, 2014; Joosse S A et al., EMBO Molecular Medicine, 2014). Moreover, CTCs have never been a direct target of a therapeutic approach.

CTCs are rather rare cells, i.e. 1-10 cells per milliliter of peripheral blood and are often genetically, phenotypically and functionally heterogeneous. These values are found in the majority of patients with solid tumors in the metastatic stage (i.e. in all those where they were analyzed/studied). In solid tumors not in the metastatic stage their frequency is even lower. They may acquire stem-like properties and change dynamically during time, converting from a more epithelial-like state to one more mesenchymal-like and vice versa, through processes known as Epithelial-to-Mesenchymal and Mesenchymal-to-Epithelial Transitions (EMT & MET). During these processes CTCs literally change their phenotype down-regulating specific antigens while up-regulating others. For example, during/through EMT, CTCs can lose the expression of one key epithelial marker, i.e. EpCAM, and acquire a pivotal mesenchymal marker, i.e. N-Cadherin, or a stemness-related marker, i.e. ABC-G2. CTCs can move inside the circulatory system singly or in clusters. Clusters possess 23- to 50-fold increased metastatic potential in respect to single CTCs (S A Joosse et al., EMBO Mol Med, 2014; M G Krebs et al., Nat Rev Clin Oncol, 2014; T Brabletz, Cancer Cell, 2012; Y Kang & K Pantel, Cancer Cell, 2013; N Aceto et al., Cell, 2014). Hence, a number of CTC populations exists, epithelial, mesenchymal, hybrid epithelial-mesenchymal, stem-like, single CTCs, CTC-clusters. All patients with solid tumors are potential CTC carriers, regardless of the stage of the disease. Therefore, potentially all solid tumors, approximately 95-98% of all tumors, have CTCs. However, only some of them will show clinically relevant blood CTC dissemination. In fact, some kind of tumor disseminate only locally and/or not preferentially through the blood vessels (e.g. head and neck cancer). Hence, only specific kind of tumor could actually benefit from the removal of CTCs from the TBV. For example, tumors that can actually benefit from the CTCs removal will be those which metastasize more through the blood vessels and that are more prone to disseminate CTCs far from the primary tumor also, such as breast and lung cancer. CTCs may also be present in the early months of the disease. From this point of view, at the clinical level and for clinical utility, avoiding its dissemination as soon as possible can be far more efficient that inhibiting their spread when the tumor has already metastasized in multiple sites. As mentioned above, CTCs are mutually phenotypically heterogeneous, i.e. the antigens expressed on their surface can be different from cell to cell, and they are capable of mutating over time. This means that during the progression of the disease they may acquire and/or lose antigens. In other words, the circulating tumor cells constitute an uncommon cell population consisting of several subpopulations defined as, for example, epithelial cells, hybrid epithelial-mesenchymal cells, mesenchymal cells, mesenchymal and/or epithelial circulating tumor stem cells; therefore, a set of biomolecular characteristics that make then extremely difficult to detect and investigate.

Despite CTC importance, all known approaches, reported in prior art, refer to methods that delve with CTCs from just a single or few points of view. Moreover, CTCs have been investigated only as markers without demonstrating their full potential. At present, no one exploit them as targets and without using any drugs that specifically target CTCs. CTCs are the "leukemic phase" of a solid tumor and hence they deserve the same importance and a similar approach reserved to the primary or metastatic tumor mass: an actual "liquid surgery".

To date, the main systems for analyzing and capturing these cells are based on their biological properties, for example by providing the use of individual antibodies directed against antigens expressed on their surface (e.g. in particular EpCAM), or physical properties, by being capable of selecting the CTCs by size or cell density, or on combinations of biological and physical approaches. However, these methods exhibit the disadvantage of selecting cells that express only one or a few epithelial antigens and especially of analyzing only small volumes of peripheral blood, normally less than 30 ml.

Regardless of the type of method chosen, in fact, in most cases, the analysis of the CTCs is always carried out on a small volume of peripheral blood, e.g. 5-10 milliliters. If on the one hand a small withdrawal of blood is cheap and poorly invasive for patients, on the other hand it considerably decreases the chances of detecting cells that are so rare. As demonstrated by Coumans et al. Clinl, Cancer Res, 2012, as the volume of analyzed blood increases, the likelihood of detecting and possibly removing the CTCs also increases. In addition, it has been demonstrated (through a mathematical extrapolation) that in 99% of patients with a metastatic tumor at least one CTC can be detected once the entire volume of blood has been analyzed, i.e. the total blood volume (TBV). The TBV is the volume of blood that usually circulate in a human being/patient. Normally this volume consists in up to about 3-5 liters. It follows that to detect and then delete the greatest number of circulating tumor cells it is necessary to analyze a volume of blood that is as large as possible.

To then perform a true liquid biopsy/surgery and therefore detect and remove the greatest possible number of CTCs, a substantial increase in the volume of peripheral blood that is analyzed, and therefore in the yield of the CTCs themselves, is required. Since it is obviously impossible to collect large quantities of blood from a patient without causing damage to him/her, one possibility is to use a method of extraction of the CTCs connected to an extracorporeal circulation system (ECS). As stated by Allard W J and Terstappen L W, Clin Cancer Res, 2015, an ECS-based system would allow for increasing the volume of analyzed blood up to at least 1 "total blood volume" (TBV), i.e. about 3/5 liters in total, if not even up to 4/6 TBVs, and thus for increasing the number of circulating tumor cells that are potentially detectable and removable.

Although devices for capturing CTCs by means of extracorporeal circulation systems and size exclusion filters suitable for the capture of tumor cells are known, these devices have the disadvantage of being able to analyze blood volumes equal to a maximum of 1 to 3 TBV and of not detecting and capturing cells that are smaller than the pores of the filter independently of the antigens expressed by the CTCs, thus obtaining only a limited yield of capture. In particular, the known devices often do not capture CTCs that express antigens other than epithelial ones. Also, these devices are stationary, motionless filters or tubes that are clearly prone to be obstructed or clogged up if many liters of blood and different cellular elements pass through them. For example, known devices are mainly targeted to just one population of CTCs, e.g. epithelial, and were generally based on microfabricated filters included in an apheretic extracorporeal circulation. It is clear that a still too small volume of blood can be screened with such devices due to the nature of the apheretic procedure (designed to screen a limited number of liters of blood) and because after a number of cycles/milliliters of blood the system will be inevitably clogged or saturated, probably inducing dangerous blood clotting also. Moreover, such filters certainly require a low blood flow speed to try to avoid early clogging and saturation.

It is an object of the present invention to overcome the above mentioned drawbacks of the known systems for detecting and capturing CTC biological and/or chemical entities and to provide a device and a method which are more efficient and functional.

DESCRIPTION OF THE INVENTION

A device, a system and a method for the removal of at least one undesirable biological and/or chemical entity from an extracorporeal blood volume are provided according to the independent claims.

The device according to the present invention comprises a hollow capture chamber having an inlet for the entry of blood from an extracorporeal system/circuit and an outlet for the outflow of the extracorporeal blood and the re-entry into the normal body circulation. The capture chamber internally comprises at least a capture element movable relative to the capture chamber and having a reactant surface which is placed in contact with the extracorporeal blood. The reactant surface comprises a plurality of binding agents for the biological and/or chemical entity to be removed such that at the outlet of the capture chamber the biological entity is removed from the extracorporeal blood, the biological and/or chemical entity being bonded to the reactant surface. In particular, the total volume of extracorporeal blood flowing inside the capture chamber is comprised between 1 and 6 TBVs and wherein each TBV consists of up to 5 liters of blood.

This device is practical and effective in its operation.

By employing the device according to the present invention, it is possible to realize an "ex-vivo liquid surgery" for removing biological entities (for example CTCs) from the blood of a patient thereby limiting or avoiding tumor progression, that is similar to a conventional surgical approach of a solid tumor that can limit the disease or even cure a cancer patient.

According to the present invention, it is possible to capture the greatest possible number of undesirable biological and/or chemical entities during their circulation in the bloodstream. Moreover, the present invention allows for analyzing a high volume of blood, even up to 300 ml/minute, a value that is much higher than any blood sampling. In fact, known systems for the analysis of CTCs, based on simple blood sampling, analyze a maximum of 1-30 ml of peripheral blood. Moreover, given the rarity of the CTCs, the chance of detecting "false negative" cases is statistically very high. Other systems can instead analyze a higher amount of blood but never reaching the volume indicated by the approach according to the present invention, most importantly, never using a device implying a dynamically driven cell-to-surface contact. Through an in vivo system for capturing CTCs, for example, said CTCs can be directly captured in a patient's vein without collecting blood from said patient. However, a system of this kind, although screening the patient's blood for about 30 minutes, can analyze no more than about 1.0/1.5 l of blood and capture the CTCs thanks to a single antibody that only binds the EpCAM molecule, if expressed on the CTCs.

Instead, the device and the system according to the present invention can screen from 3 to 5 liters of blood (=1 Total Blood Volume [TBV]) up to about 30 liters of blood, i.e. 4/6 TBVs, practically identical to or even greater than what is obtained with a traditional ECS system, for example, leukapheresis or hemodialysis for renal disease or failure.

In a particular embodiment of the present invention, to increase the possibility to catch all the CTCs, the TBV is examined more than one time, up to at least about 14 times (14 TBVs), that is to say up to about 72-74 liters of blood. In this way, the device of the present invention allows the capture of CTCs from up to about 14 TBVs of a cancer patient in order to allow the recovery of a highly significant amount of CTCs. The recovery of a highly significant number of CTCs will allow statistically significant clinical information (after downstream cellular and molecular analysis), allowing critical clinical decisions and personalized medicine approaches.

The removal of CTC sub-populations, epithelial, mesenchymal and/or hybrid, singly or in clusters, is obtained by the combination of molecular (antigen expression dependent) and physical (size dependent) approaches. The device according to the present invention can comprise a number of different binding reagents targeted towards CTC-specific antigens. In particular it comprises EpCAM, E-Cadherin, N-Cadherin, CD44 and its isoforms (e.g. CD44v6 and CD44v8), selectins, ABC-proteins, MUC1, FGFRIIIc, and other "every kind of target/antigens" related to epithelial, mesenchymal and cancer stem-like phenotypes. At least, 5 to 6 binding molecule type are necessary to enrich and grab most of the CTC populations. Preliminary data, confirmed that the selection of the previously reported CTC-specific antigens herein presented is optimal. With this combinatorial approach, in fact, epithelial, mesenchymal and/or hybrid CTCs have been detected in cell line models during EMT and in particular in cancer patients during progression also. These results clearly demonstrate the efficiency of the device and the method according to the present invention.

In fact, thanks to the use of a plurality of binding agents (at least 6 antibodies) distributed on the reactant surface, a greater number of entities to be removed can be intercepted, as they are directed to a greater number of antigens expressed by such entities. Hence, all the CTC sub-populations, epithelial, mesenchymal and/or hybrid, singly or in cluster are targeted and captured by the device. Specifically, the device serves as a trap for the circulating entities to be removed, which by interacting with the plurality of binding agents on the reactant surface of the capture element, remain bound to this surface and do not continue along the bloodstream's path of the blood flow. The blood exiting the device will therefore be devoid of the undesirable entities. At a later time, these removed entities can be collected from the surface of the capture element and analyzed downstream to support clinical decisions through clinically relevant data related to their nature. Hence, in its various embodiments, the device according to the present application is aimed at treating cancer, removing them from blood, and enriching CTC allowing further downstream analysis. In turn, these analyses allow a significant monitoring of cancer features, during progression also, giving to the clinician a statistically significant number of cancer cells to be studied.

The shape and the size of the capture chamber and capture element are such as to allow for a flow of blood therein up to about 200-300 ml/minute and to ensure the largest possible contact surface between the filter element and the blood flow.

For example, two types of devices and thus of capture chambers are conceivable: a microscopic one and a macroscopic one.

The microscopic device can provide a minimum length of 2.0 cm and a minimum diameter of about 1.2 cm, while the macroscopic device can provide a minimum length of between 4.0 and 5.0 cm and a minimum diameter of about 1.2 cm. Of course, different dimensions are conceivable on the basis of appropriate hemodynamic studies.

The feature according to which the capture element is movable relative to the capture chamber allows capturing the undesirable biological entities (i.e. CTCs) and helping these entities to get as close as possible to the reactant surface of the device (able to catch/grab the CTCs). In fact, due to the mobility of the capture element, the reactant surface is better in contact with the blood flowing during the extracorporeal phase of an extracorporeal circulation procedure. Moreover, the moving structure can be headed and/or followed, in the direction of the blood flow, by a filter structure.

The movement of the capture element, that represents the core structure of the device, can be guided by the blood flow or by an external force. The movement, in turn, will lead to a stirring of the blood and to a circulating path in the chamber increasing the contact of cells with the reactant surface and the internal wall of the capture chamber. This movable element also facilitates the fluid circulation, making easier to capture numerous TBV, without the risk of system clogging or blood clotting and damage.

The undesirable biological and/or chemical entity to be removed can be any cell, undesirable entity or pathological biochemical structure noxious for the human body, which can be detected within the blood and has specific recognizable traits. Specifically, this element can be a circulating tumor cell (CTC). In this way, through the device according to the present invention, the spread of the CTCs in a patient's body, and consequently the development and growth of metastases, can be prevented, or at least greatly reduced. The device can potentially target all solid tumors, i.e. more than 95% of tumors. However, as already mentioned, some types of tumors are more prone to distant dissemination through blood vessels and hence they are more biologically and clinically suitable for the use of the device according to the present invention in its various embodiments.

Summarizing the above, by using the device according to the present invention. it is possible to combine for the first time the examination of up to 6 TBVS or up to 14 TBVs with three different and complementary approaches: a molecular, a physical and an engineering-based fluid dynamic approach, the last of them being a first in art method to capture CTCs. This combination approach ensures a) a higher level of capture efficiency, providing the removal of epithelial, mesenchymal, hybrid epithelial-mesenchymal, and stem-like CTCs, singly and/or in clusters, b) a sustained and reasonably fast blood flow and c) no risk of system clogging or blood clotting and damage.

The binding agents are distributed on the surface of the capture element in order to capture the undesirable elements within the bloodstream by binding to antigens, proteins or receptors on the surface of the undesirable entity to be removed. Specifically, the binding agents may comprise one or more antibodies, adhesion proteins, aptamers, oligo-aptamers, or other organic molecules specifically directed against any undesirable compound or element that must be removed from the bloodstream. In the case of CTCs, these are captured by the binding agents due to the presence of antigenic epitopes on the membrane of the tumor cell, which depend on the subpopulations of the target cells, for example, epithelial cells, hybrid epithelial-mesenchymal cells, mesenchymal cells, mesenchymal and/or epithelial circulating tumor stem cells (singly or in clusters) and/or any other CTC subpopulation that can be detected in the blood of cancer patients. The collection of different subpopulations of cells can be obtained thanks to suitable and customizable mixtures of antibodies and/or molecules recognized as binders for the cells of interest. These mixture of capturing molecules can be different from cancer to cancer, from patients to patients, depending on the antigens present on the CTCs. The discovery and selection of the more suitable antigens with which functionalize the surfaces of the device can depend on the discovery or investigation of specific antigens on the primary/metastatic tumor tissue or utilizing a liquid biopsy approach (e.g., Cell Search, DEPArray, ISET, etc., . . . ). To increase the likelihood of capture, binding agents or antibodies directed against alternative antigens/phenotypes expressed by the CTC cells to be removed may be used, i.e. in addition to those traditionally recognized, as well as those identified more recently and characterizing the CTCs deemed more aggressive (Barriere G et al. Ann Transl Med 2014).

To optimize the capture of the entities to be removed, the binding of the antibodies and/or other biological biomolecules or binding agents must be such that their antigen-binding moiety (e.g. Fab for antibodies) is positioned with an orientation that goes from the surface of the capture element in the direction of the inner surface of the capture chamber. In this way, the likelihood of binding to the analyte (for example the CTCs) can be maximized.

The capture of undesirable entities within the bloodstream can be achieved by means of specific techniques, such as controlled immobilization (Qian W et al., Clin Chem. 2000; Jung Y et al., Anal Biochem. 2008; Kumada Y, Biochim Biophys Acta 2014; Crivianu-Gaita V and Thompson M, Biosens Bioelectron 2015).

Advantageously, Fab fragments of an antibody alone may be immobilized. Compared to the more traditional technique of immobilization of the whole antibody, the binding of Fab fragments proves to be able to reach higher surface densities, thereby obtaining a higher binding capacity for the analyte (Crivianu-Gaita V and Thompson M Biosens Bioelectron 2015).

The type of binding of the antibody/Fab to the surface can be determined on the basis of the material chosen for the reactant surface of the capture element. The immobilization of antibodies/Fab fragments can be, for example, carried out on gold (Au)-coated, silicon (Si)-based, and polysaccharide-based surfaces, or on plastic and generally inorganic, yet always biocompatible, surfaces like polyurethane, polypropylene and/or polycarbonate.

The possibility to functionalize the device with different binding agents, i.e. antibodies, depending on the disease, is of particular interest. In fact, it is conceivable that a first group of antibodies is potentially present on each device and directed against antigens expressed by a subpopulation consisting of CTCs, while a second group can be selected on the basis of the disease under examination.

Specifically, by way of example, EpCam (CD326), E-Cadherin (CD324) and EGFR (epitheliality), N-cadherin (CD325) and OB-cadherin (cadherin 11) (mesenchymality) can be considered as "standard" antigens, and at least, for example, CD44v6 (colon cancer; tumor stemness), CD44v8 (breast cancer; tumor stemness), Her-2 (breast cancer) and ABC-G2 (tumor stemness) as "disease-specific" antigens.

It should be noted that both the different binding agents and the shape of the device itself, and in particular the shape of the reactant surface as well as the mobility of the capture element relative to the capture chamber, affect the action of capture of the entities to be removed, for example the CTCs. In fact, the binding agents detect and capture various subpopulations of entities to be removed, while the shape and the movement of the reactant surface allow for increasing the contact surface as well as the contact probability between the capture element and the blood of the patient, thereby allowing for a greater likelihood of binding between the entities and the different binding agents.

The capture chamber of the device according to the present invention is hollow and must have a shape that allows the blood flow to circulate inside it in a fluid and smooth way. In one embodiment of the invention, the capture chamber has a cylindrical shape and the central movable capture element extends longitudinally within the capture chamber. Both the capture chamber and the capture element can be entirely made up of an alloy or material biocompatible with a coating such as to prevent a possible interference with coagulation, normal blood cells or other physiological processes. In order to promote adhesion of the undesirable biological and/or chemical entities onto the reactant surface of the capture element, said surface can be advantageously coated with a thin layer of gold or other biocompatible material. In addition, in order not to impair the blood flow, the reactant surface of the capture element may be made of a deformable material.

In one embodiment of the invention, the movable capture element can rotate about a longitudinal axis of the capture chamber. This allows for maximizing the contact surface between the reactant surface of the capture element and the blood flow containing the undesirable entities to be removed. Furthermore, the rotation of the capture element allows the blood to flow away better, thereby avoiding system clogging and/or blood damage and clotting. In fact, the continuous movement can help to maintain the fluidity of the blood and prevent the formation of clots. The movement of the central element can also be allowed by the presence of four, preferably small, magnets, two positioned at its ends and two at the ends of the capture chamber. The magnets thus positioned will maintain the central element in levitation, thereby reducing the possible friction that could be created between the central element and the outer chamber.

An anticoagulant, such as heparin, can also be added in order to prevent unwanted coagulation phenomena. The movement and the anticoagulant have the purpose of maintaining the blood characteristics intact, thus allowing for the maintenance of the clinical safety of the patient.

To further increase the safety of the patient, the blood pressure can be controlled both in the input and output of the capture chamber such that it remains even.

The rotation of the capture element relative to the capture chamber around a longitudinal axis can take place either by the mere effect of the blood flow, and therefore without the application of a dedicated external force, or by application of an externally regulated, continuous driving force.

The rotation of the capture element is pivotal to allow a better capture competence of the overall device in respect to an apparatus without rotating elements. This data depends on the capability of the rotating capture element to help the target CTCs to get in proximity with the reactant surface of the device.

In order to allow the undesirable entities captured by the reactant surface to be analyzed, the capture element can be removed from the capture chamber. This may be accomplished by means of a coupling/uncoupling system located at the entrance and at the exit of the capture chamber.

Moreover, the binding agents are linked to the surface of the device utilizing biochemical linkers able to be cleaved only when the procedure has been stopped and the device taken outside from the EC. This detail allows the recovery of cells from the device in order to study them and obtain clinically useful information with cellular and molecular methods already known.

In one embodiment of the invention, the reactant surface of the capture element comprises a helical structure. In particular, the helical or screw or Archimedes' screw structure extends longitudinally around a rotation axis and is secured to the capture chamber by means of a fastening system. More specifically, the movable capture element is shaped like an helix or spiral. This particular shape is used to ensure an even flow of the blood fluid and at the same time a greater surface that is in contact with the circulating blood so as to increase the likelihood of binding between the entity to be removed, for example the tumor cell, and the binding agents, for example the antibodies. Preferentially, the helical surface may extend along the entire length of the capture chamber. However, a configuration in which the length of the helix is less than the length of the capture chamber and inside which there is a plurality of helical structures placed in series may also be used. Of course, through such a configuration, the length of the entire device must be necessarily increased.

According to the embodiments of the present inventions, the movable capture element is configure to facilitate the contact between the reactant surface of the device and the target cells. Hence, every kind of moving helix, double helix, or other moving 3D structure made up to facilitate this contact is included in this invention.

According to the microscopic type mentioned above, the device may, in particular, have a minimum diameter of between 0.5 and 0.8 cm per single helix, in which the helix can perform 5 rotations around its central axis, i.e. approximately one each 0.4 cm.

According to the macroscopic type mentioned above, the device may have a minimum diameter of between 0.5 and 0.8 cm per single helix, in which the helix can perform 5 rotations around its central axis, i.e. approximately one each 1.0 cm.

In particular, the movable capture element of the device, first in art in the field of CTC study, is a rotating system with the aim of driving cells as near as possible to the reactant surface and of that of internal wall of the capture chamber. In an embodiment of this invention, the capture element is similar to an Archimedes screw, including all different shapes, dimensions and types of helices or similar 3D moving structures and appropriate capture chambers or housing tubes. The rotational speed is controlled by the blood flow through the chamber depending from a CEC system. The flow speed can be adjusted in order to throw/cast blood cells and CTCs towards/on the surface on the same moving capture element and/or on the surface of the internal wall of the capture chamber. At this stage of the procedure, cells hit the reactant surface of the helix. Cells can be captured at this point or driven by the thrust of the moving capture element itself towards the internal wall of the chamber. In this system, several rounds of total blood can be screened to obtain a maximum capture efficacy as already mentioned. A device having a rotating capture element helps therefore to obtain a maximum capture effectiveness.

In another embodiment of the invention, the device further comprises one or several conical structures consisting of thin cables made of biocompatible material. These structures have a filtering mesh surface made of holes (pores) with a diameter greater than 100 µm. The conical structure can be positioned upstream or downstream the capture element and in line with this element. The conical structure may be similar, for example, to a spider filter for the protection from distal and vascular emboli. In particular, the capture element can be configured so as to comprise a single conical structure that is fixed or can rotate around a longitudinal axis passing through the tip of the cone, in which the base of the cone receives the input blood flow. However, to improve the filtering effect, the capture element may be configured so as to comprise a plurality of conical structures positioned in series along the direction of the blood flow.

This conical web filter is technically designed to block very large CTCs but in particular tumor micro emboli or CTC-clusters. These elements possess higher metastatic potential with respect to single CTCs. Hence, the "spider filter" like filters plays a pivotal role in preventing the dissemination of blood micro emboli, limiting metastatic relapse and increasing device safety.

The pore diameter has been selected to block CTC clusters, but large enough to avoid risk of system clogging or blood clotting and damage. The selection of a diameter of about 60 to 100 micrometers has a further justification. CTC-clusters are born from oligo-clonal tumor cell groupings and not from intravascular aggregation event (Aceto N. et al., Cell, 2014). Hence, accepting a cell cluster is composed of 2 or more cells (range from 2 to 19, average 10.5, as reported by Sarioglu A F et al., Nat Methods, 2015) and assuming that single CTC diameter ranges from 8 to 16 micrometers, 12 in average (Hosokawa M et a., PlosOne, 2013; Patrizia Paterlini-Bréchot, Cancer Microenviron 2014; Vona G et al., Am J Pathol. 2000), it can be inferred that an average cluster of about 10 cells presents a dimension around 120 micrometers (range from 96 to 160).

In a further embodiment of the invention, the device may comprise a combination of a capture element having a helical structure with one or more conical structures. This allows for further enhancing the performance of capturing the entities to be removed as well as the clinical safety of the device since it may block potential clots and emboli. In particular, such a device may be configured so that the helical structure precedes the conical one, referring to the direction of the blood flow.

One embodiment of the invention can provide for the presence of multiple complete devices (capture chamber and central capture element) positioned in series like the pearls of a necklace.

The core structure of the device, that can be the helix element combined with a web-like filter, can be coated with molecules targeted towards CTC-specific antigens in order to specifically catch them during their flow through the device.

Of course, alternative forms to the helical or conical ones as regards the reactant surface of the capture element are possible and fall within the invention. The important thing is that the shape is such as to ensure, on the one hand, a good surface of contact with the blood flow, and on the other, a fluid blood flow without the risk of clots, emboli or block system.

Advantageously, the plurality of binding agents is distributed evenly over the entire reactant surface of the movable capture element. This allows the capturing action to be distributed over the entire reactant surface of the capture element.

Alternatively, the binding agents can be concentrated in specific areas of the reactant surface of the movable capture element. This is particularly advantageous when using binding agents of a different nature. In other words, a "progressive" distribution of the binding agents on the reactant surface is possible. This means that the binding agents, for example the antibodies, directed against certain antigens can be placed only at one end of the reactant surface, while the remaining may adhere to other adjacent regions. This configuration, other than allowing for an efficient capture capacity, allows the entities to be detected in a more simple way. In fact, once the capture element has been removed, the entities can be easily identified by analyzing the different regions of the reactant surface that are specific for different subpopulations of entities to be removed.

In a further embodiment of the invention the binding agents are distributed evenly or only concentrated in specific areas on the inner surface of the capture chamber. In this way, it is possible to increase the capture action of the device. More specifically, the distribution of the binding agents on the internal surface of the capture chamber as well as on the reactant surface of the capture element allows that a higher quantity of blood is treated by the device.

The moving capture element, the conical filter and the internal wall of the capture chamber can all have reactant surfaces. These surfaces are coated with multiple binding agents directed towards different CTC antigens and consequently towards different CTC populations. According to this configuration, the total volume of blood exiting from the capture chamber, passed through the device, is cleaned of CTCs, the CTCs being captured by the internal reactant surfaces of the device. By repeating this approach a number of times (6 up to 14 times), for up to about 4 to 5 hours at a blood flow speed up to 300 ml/min, it is possible to screen up to 14 TBV per treatment with the aim to remove more than 90/95% of CTCs from the TBV.

As already mentioned, the various embodiments of the present invention can comprise one or more capture chambers (housing tubes plus the internal moving elements plus the conical "spider" filters) organized in sequence. Each single capture chamber is coated, on its internal surfaces, with one or more types of binding molecule (e.g. antibodies or aptamers) against all the known CTC sub-population (epithelial, mesenchymal and/or hybrid, singly or in cluster). In another embodiment of the present invention, at least 3 or 4 chambers are foreseen. The different chambers are organized in sequence following the direction of the blood flow. Each chamber is coated with binding molecules against a specific type of CTC sub-population (e.g., the first chamber against mesenchymal CTCs, the following chamber against epithelial CTCs and the last chamber against cancer stem-like cells).

It is noted that the possibility to analyze up to 6 TBV or up to 14 TBV of patient's blood is guaranteed by the fact that the capture element can move, i.e. can rotate around its longitudinal axis in blood flow direction, and/or by the fact that conical structures are present acting as filters for clusters of cells and/or by the fact that the binding agents are not only present on the surface of the capture element but also on the internal surface of the capture chamber and/or on the surface of the conical structures.

The system for the removal of biological and/or chemical entities according to the present invention is based on the integration of the removal device mentioned above into an extracorporeal circulation system, similar to therapeutic leukapheresis or hemodialysis.

In particular, the system comprises extraction means for extracting venous blood from a patient's vascular system and input means for introducing the extracted blood into the removal device. In order to extract the filtered blood from the device and complete the cycle, the system further comprises output means and re-entry means for reintroducing the blood extracted from the device—and thus filtered—into the patient's vascular system.

Moreover, to prevent the formation of clots and to keep the temperature of the blood flow under control, the system comprises a means for introducing an anticoagulant upstream of the removal device and a temperature control unit downstream of said device.

This system is capable of capturing and then removing any undesirable biological and/or chemical or biochemical entity, such as for example the CTCs, from the blood of a patient along the path travelled by these entities within the blood circulatory system. When the entities pass through the removal device, said entities (for example CTCs) are retained by the binding agents (for example the antibodies) placed on the reactant surface of the capture element. Other types of entities or blood cells, instead, may continue their path within the circulatory system. The passage of the blood to be analyzed and filtered through the removal device takes place for a predetermined value of blood volume, after which the extracorporeal circulation system is removed, as well as the device. The latter can be opened and the entities can be directly examined on the reactant surface of the capture element, or removed from it for further molecular assessments.

Advantageously, once functionalized with the selected binding agents, the device can be assessed, i.e. tested, through the provision of an in vitro flow apparatus that mimics the circulation of a known volume of blood ex vivo or of any synthetic substance behaving like blood. This apparatus will enable for investigating the interaction of entities to be removed, for example "model" tumor cells, with the functionalized device and for simulating the in vivo venous blood flow conditions in vitro. The flow can be sustained by a peristaltic pump to allow the blood to repeatedly interact with the functionalized device. Such an apparatus entails the use of a blood sample (taken from a healthy donor) added with entities to be removed, such as for example tumor cells from established tumor cell cultures with characteristics similar to those of the CTCs, epithelial, mesenchymal, hybrid epithelial-mesenchymal, and stem-like CTCs, singly and/or in clusters. To prevent mechanical damage to the cells, the blood must not pass through the peristaltic pump. Specifically, the blood of the healthy donor—no more than 300/500 ml—is passed several times through the ex vivo apparatus and the device until reaching a TBV that is reasonably similar to what could be achieved in a patient. This apparatus will also be used to understand which capture element or combination of capture elements in terms of shape, arrangement and quantity, has the best abilities of selecting and capturing the entities to be removed (CTCs), while maintaining the normal characteristics and fluidity of the blood. For example, such an apparatus will be extremely important to understand if the device induces formation of clots or cell clusters which might affect the clinical safety of the device.

The ex-vivo method for removing at least one biological and/or chemical entity from a volume of extracorporeal blood of a patient according to the present invention comprises the steps of introducing the extracorporeal blood into a hollow capture chamber internally comprising at least one capture element, wherein the capture element is movable relative to the capture chamber, filtering the extracorporeal blood by contact with a reactant surface of the movable capture element comprising a plurality of binding agents for the biological and/or chemical entity to be removed, and extracting the extracorporeal blood devoid of said biological and/or chemical entity from the capture chamber.

In particular, the total volume of extracorporeal blood (B) flowing inside the capture chamber (10) is comprised between 1 and 6 TBVs and wherein each TBV consists of up to 5 liters of blood.

To increase the possibility to catch all the CTCs, the TBV is examined more than one time. In particular, according to the present invention the TBV is screened more than one time, up to at least about 14 times (14 TBVs), that is to say up to about 72-74 liters of blood. In this way, the method of the present invention allows the capture of CTCs from up to about 14 TBVs of a cancer patient in order to allow the recovery of a highly significant amount of CTCs. The recovery of a highly significant number of CTCs will allow statistically significant clinical information (after downstream cellular and molecular analysis), allowing critical clinical decisions and personalized medicine approaches.

The method further comprises the step of stopping the introduction of extracorporeal blood into the capture chamber after introducing a predetermined volume of blood, and removing the capture element to analyze the nature and quantity of the biological and/or chemical entity removed and present on the reactant surface.

The method therefore comprises passing the blood of a patient through a device or system described above, simultaneously contacting the blood with the reactant surface of the capture element of the device, consequently contacting it with the selected appropriate binding agents or antibodies. The step of adhesion of the binding agents to the entities to be removed can occur by means of various controlled immobilization techniques.

Therefore, the method successively comprises the step of temporary removing the venous blood from a patient's vascular system through an extracorporeal circulation system, the step of adding heparin (or other similar anticoagulant) to prevent unwanted coagulation phenomena, the step of introducing the blood into the device, thereby contacting the blood and hence the entities to be removed (for example CTCs) present in the blood of the patient with the selected binding agents for a predetermined period of time, the step of adding an effective amount of i.e. protamine to reverse the action of heparin when the treatment is finished and the final step of re-introducing the blood into the patient's vascular system.

The actual treatment time according to the method of the present invention can vary but depends approximately on the time it takes 4 or 6 TBVs to pass through the device or up to 14 TBVs. In particular, the method provides for analysis and capture of up to 5 liters or up to 72-74 liters of blood, i.e. approximately 300 ml/min. The treatment time of such a quantity of blood can therefore approximately vary between 20/30 minutes and 3 to 4 hours.

It should be noted that the device, and hence the system according to the present invention, can be used both in a phase that is immediately successive the diagnosis and also in the monitoring of the progression of the disease and of the response to possible therapies. In the metastatic and/or terminal phase, the device, may increase the time to progression, progression free survival and/or improve the quality of life of patients with tumors. The device can also be used as a "curative" device thanks to its properties of removal of undesirable entities, such as the CTCs responsible for the metastatic spread.

BRIEF DESCRIPTION OF THE DRAWINGS

These and other aspects of the present invention will become more apparent in the light of the following description of a few preferred embodiments described below.

FIG. 1 is a schematic representation of the device 1 for the removal of at least one undesirable biological and/or chemical element C (not shown in the figure) from an extracorporeal blood volume B. In particular, the device is suitable for the removal of circulating tumor cells. The device 1 essentially consists of a capture chamber 10 having an inlet 12 for the entry of the extracorporeal blood B and an outlet 14 for the outflow of the blood B. As can be seen from the comparison of FIGS. 1a and 1b, the capture chamber has a hollow cylindrical shape and the blood B flows through the cavity of circular cross-section.

Inside the capture chamber 10 there is the capture element 20; 20'; 20", which, thanks to the presence of a reactant surface (not shown in the figure) placed in contact with the blood B, is able to capture and remove the undesirable biological and/or chemical entity C from the bloodstream B.

Figures 1A, 1B:
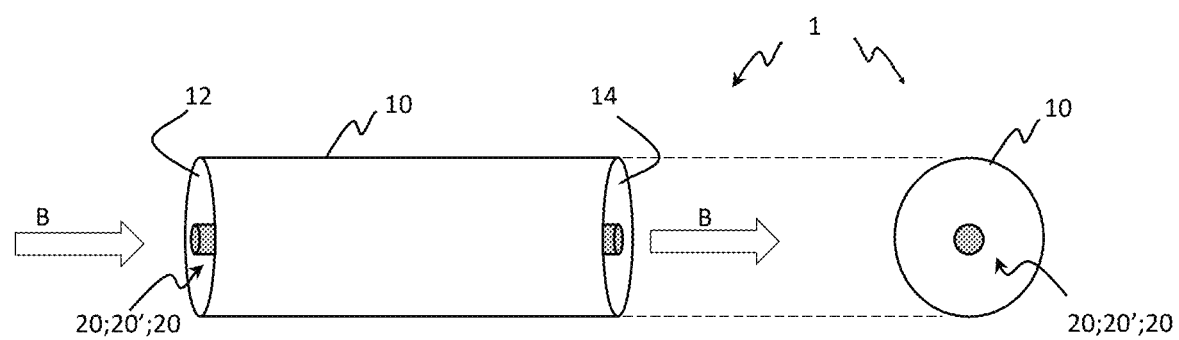
FIGS. 1a and 1b are schematic representations of the device according to the present invention in a longitudinal view (a) and in cross section (b)
Figure 2:
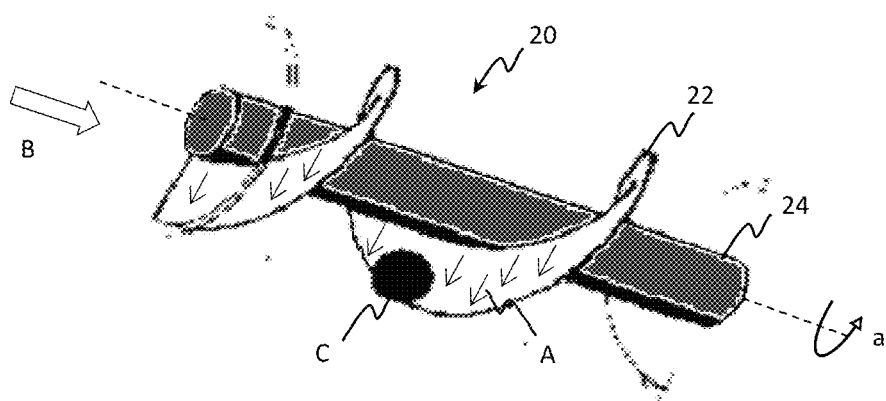
FIG. 2 is a schematic representation of a capture element according to an embodiment of the present invention.

FIG. 2 shows an embodiment of a capture element 20 to be placed inside the capture chamber 10. This consists of a longitudinal element 24 parallel to the longitudinal axis a of the capture chamber 10 around which a helical-shaped reactant surface 22 is wound. Specifically, the reactant surface 22 has the shape of an Archimedes' screw. The binding agents A (represented in the figure by arrows) are distributed on the reactant surface 22, the which agents are used to capture the biological and/or chemical entity C to be removed, represented by a circulating tumor cell. As can be seen in the figure, the capture element 20 can rotate around the longitudinal axis a of the capture chamber 10. This rotation is caused by the blood flow B which drives the reactant surface 22 into a helical motion. In this way, each part of the reactant surface 22 can come into contact with the blood flow B.

Figure 3:
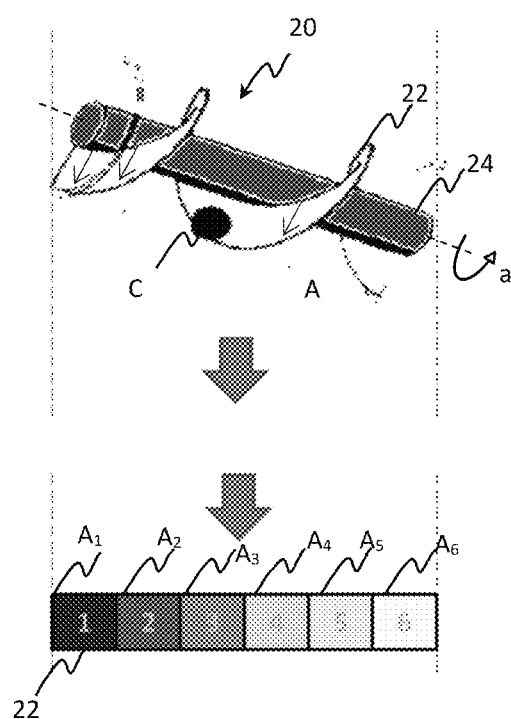
FIG. 3 is a schematic representation of the capture element of FIG. 2 with a progressive distribution of the binding agents on the reactant surface.

FIG. 3 shows the particular case in which the binding agents are distributed in a circumscribed manner in certain regions of the reactant surface 22 of the capture element 20. In particular, the figure shows six different rectangular regions defined on the helical-shaped reactant surface 22, which in FIG. 3 is arranged on a single plane for reasons of clarity. Each of the six regions displays a binding agent A of a different nature ($A_1$, $A_2$, $A_3$, $A_4$, $A_5$ and $A_6$), so that different subpopulations of tumor cells C (in this case six) associated with different antigens may be simultaneously captured and localized on the reactant surface 22 in an easier and faster way. Alternatively, the different types of binding agents can be adhered to the central device with an even concentration but not located on specific surfaces, i.e. by distributing them homogeneously over the entire surface of the device or on the internal wall of the capture chamber.

Figures 4A, 4B:
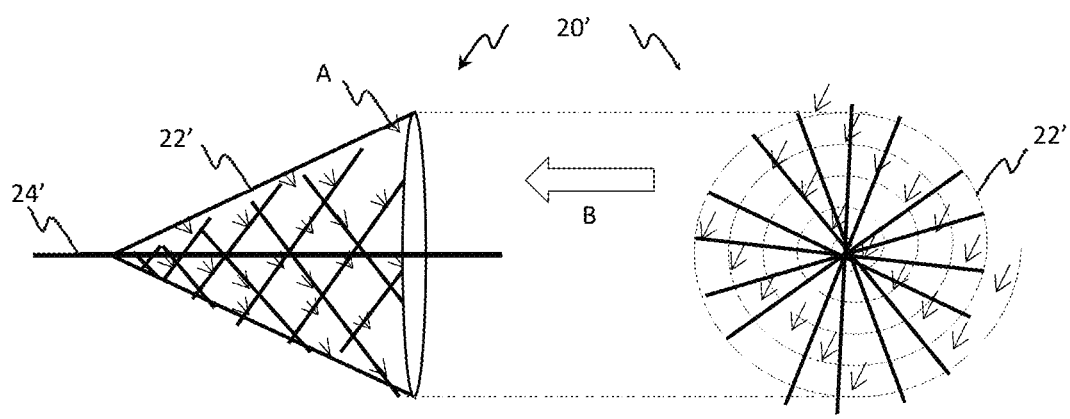
FIGS. 4a, 4b, 4c and 4d are schematic representations of a capture element according to a second (a, b) and a third (c, d) embodiment of the present invention in a longitudinal view (a, c) and in cross section (b, d)
Figures 4C, 4D:
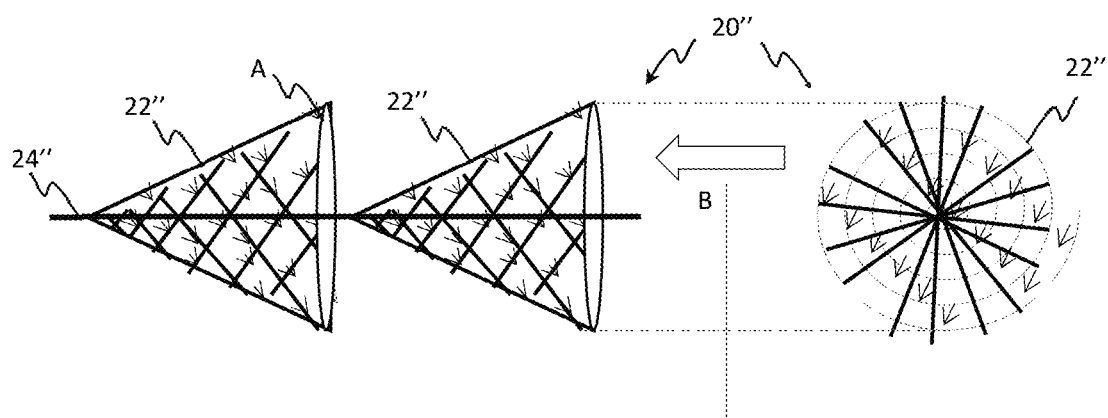

FIG. 4 shows another embodiment of a capture element 20'; 20" to be placed inside the capture chamber 10. According to this embodiment, the capture element 20'; 20" has a conical structure and is positioned inside the capture chamber 10 so that the blood flow enters through the base of the conical structure. The capture element may comprise a single conical structure 20' (FIGS. 4a and 4b) or a plurality of conical structures 20". Specifically, FIGS. 4c and 4d show the case in which two conical structures are placed in series in the direction of the blood flow B. The conical structure 20'; 20" of this embodiment, in particular, consists of thin cables made of biocompatible material onto which the binding agents A adhere. The conical structure 20'; 20" has a circular base and extends symmetrically around a longitudinal element 24'; 24" parallel to the longitudinal axis a of the capture chamber 10.

Figure 5:
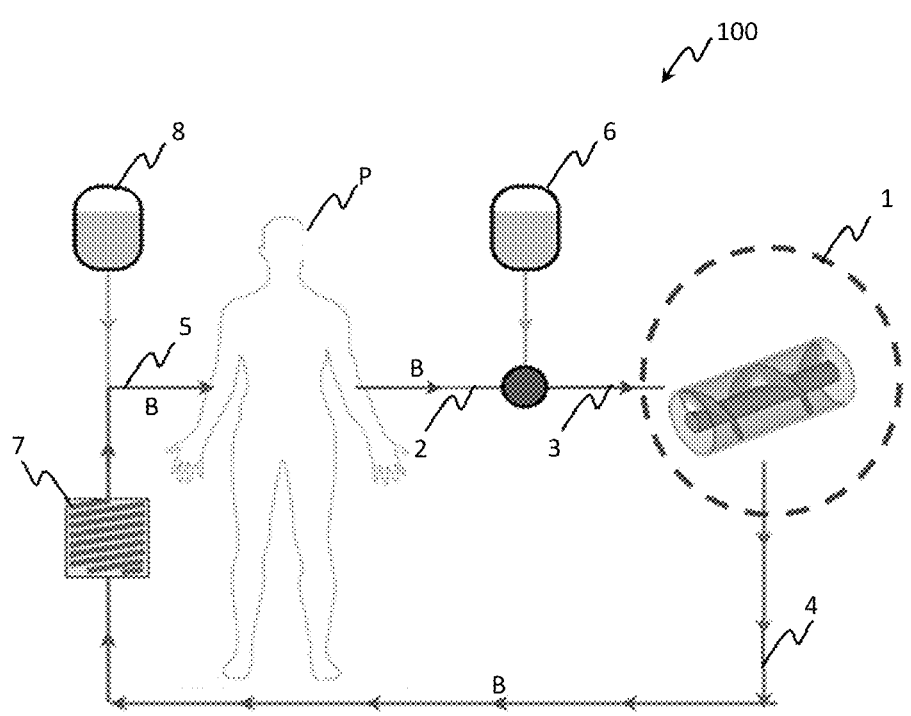
FIG. 5 is a representation of an extracorporeal circulation system according to the present invention.

FIG. 5 shows an extracorporeal circulation system 100 according to the present invention. Through a system of cannulae 2 the blood B can be extracted from the vascular circuit of a patient P and through another system of cannulae 3 it can be introduced into the removal device 1. A means 6 for the introduction of an anticoagulant is inserted between the two systems of cannulae 2 and 3. After passing inside the device 1, the blood B can be extracted through suitable dedicated means 4, and by passing through a temperature control unit 7, reintroduced through a new system of cannulae 5 into the body of the patient P. An appropriate means 8 for the reintegration of fluids, for example for neutralizing the effect of the anticoagulant, is inserted in the vicinity of the system of cannulae 5 for reintroducing the blood B.

Figure 6:
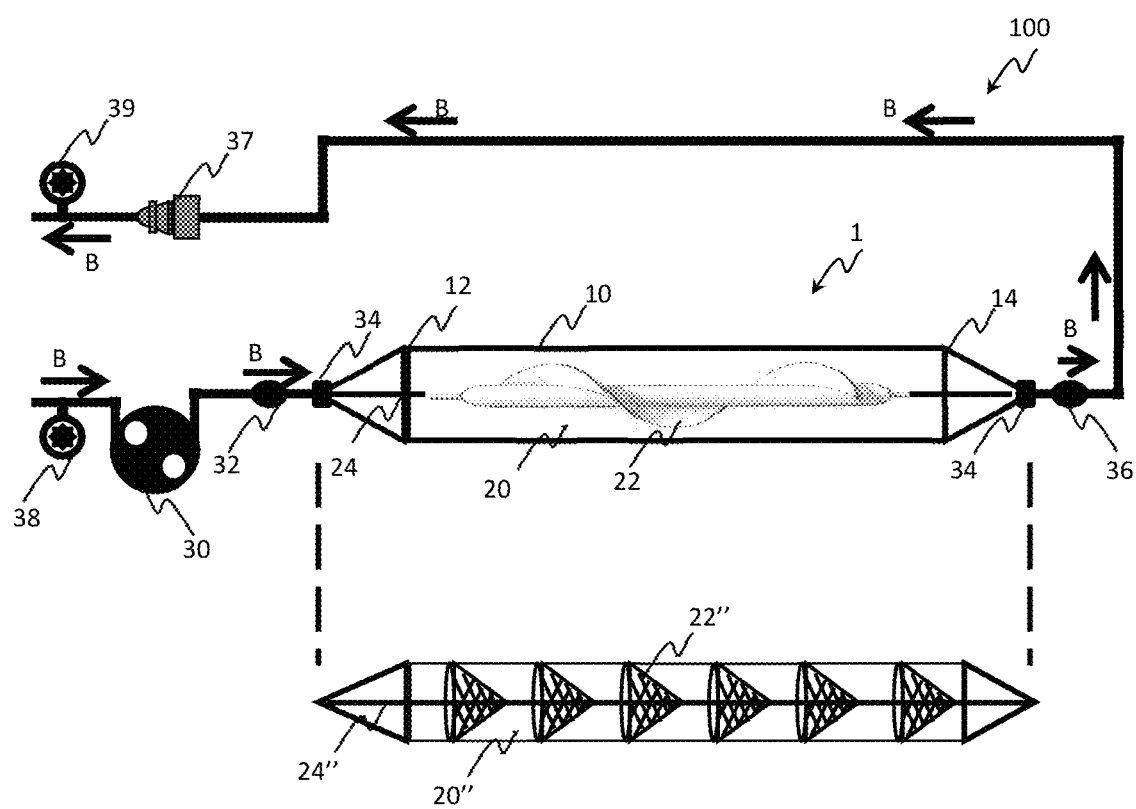
FIG. 6 shows a detail of the extracorporeal circulation system according to an embodiment of the present invention.

FIG. 6 shows a detail of the system 100 with regard to the inlet 12 and the outlet 14 of the capture chamber 10 of the device 1. Specifically, the system comprises a pump for the extracorporeal circulation 30, an inlet valve 32 and outlet valve 34 for the entry into and the exit from the capture chamber 10, two manifolds 34 at the inlet 12 and the outlet of the capture chamber 10, an air detector 37 downstream of the device 1 and a detector for the inlet pressure 38 and a detector for the outlet pressure 39. FIG. 6 shows, inside the system 100, a device 1 comprising a capture element 20 with a helical reactant surface 22. However, this is removable and replaceable by a different capture element 20" comprising a plurality of conical structures 22".

Figure 7:
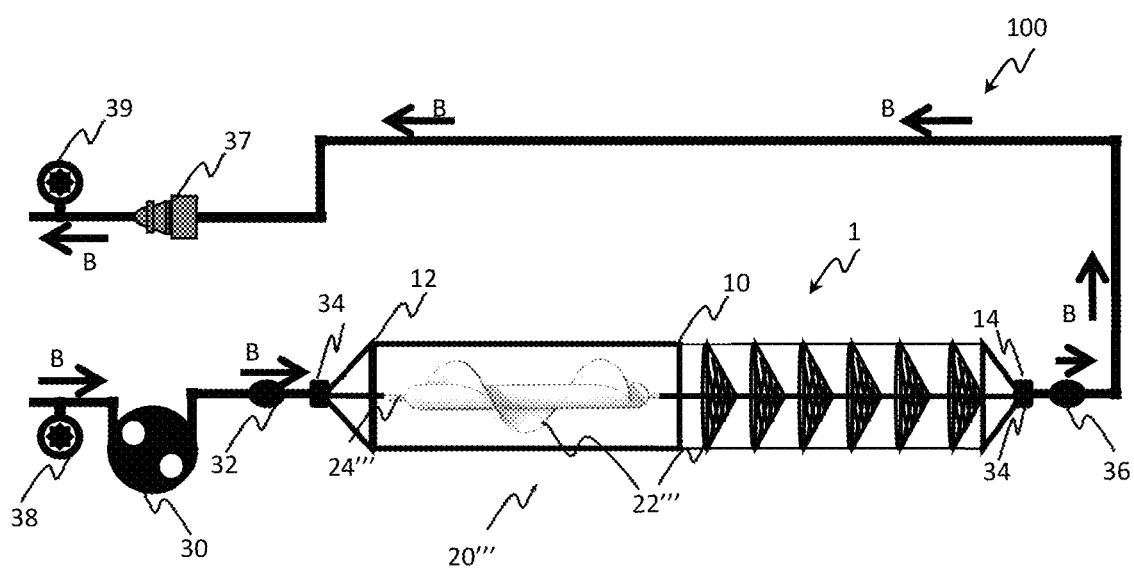
FIG. 7 shows a detail of the extracorporeal circulation system according to another embodiment of the present invention.

FIG. 7 shows a detail of the system 100 with regard to the inlet 12 and the outlet 14 of the capture chamber 10 of the device 1 according to an alternative embodiment. In particular, the disclosed system is very similar to the one shown in FIG. 6, the only difference being that the capture element 20''' consists of a helical structure followed by a plurality of conical structures. Therefore, the reactant surface 22''' is defined by a combination of conical and helical surfaces, thus increasing the chances of capture of the cells to be removed by the device 1. Moreover, the combined presence of conical structures increases the clinical safety of the device 1 since it may block potential clots and emboli.

Figure 8:
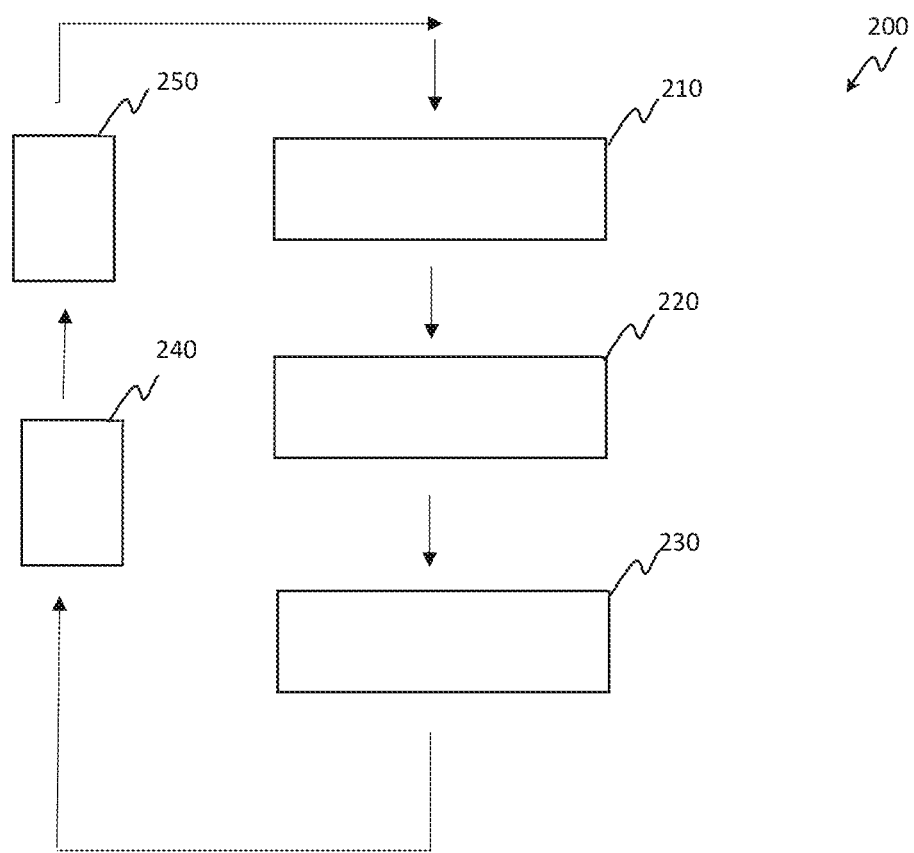
FIG. 8 schematically shows a flow diagram of a method according to the present invention.

Lastly, FIG. 8 shows a block diagram describing the method 200 for the removal of at least one biological and/or chemical entity C from an extracorporeal blood volume (B) according to the present invention.

The method 200 comprises the step of introducing 210 the extracorporeal blood B into the capture chamber 10 of the device 1 having in its interior at least one capture element 20; 20'; 20". Subsequently, the method comprises the step of screening 220 the extracorporeal blood B by contact with the reactant surface 22; 22'; 22" of the capture element 20; 20'; 20" comprising a plurality of binding agents A for the biological and/or chemical entity C to be removed. Finally, the method comprises the step of extracting 230 the extracorporeal blood B devoid of said biological and/or chemical entity C from the capture chamber 10.

The steps 210, 220 and 230 may be carried out after analyzing a predetermined volume of blood B. Above this value of blood volume B, the method 200 comprises the step of stopping 240 the introduction of extracorporeal blood B into the capture chamber 10 and removing the capture element 20; 20'; 20" to analyze the nature and quantity of the biological and/or chemical entity C removed and present on the reactant surface 22; 22'; 22". Finally, in a subsequent step 250, the capture element 20; 20'; 20", once cleared of the entities previously captured, can be reintroduced into the capture chamber 10 and the method 200 can be restarted from step 210. It should be noted that on the basis of the analysis of the entities captured in step 240, the capture element 20; 20'; 20" may be replaced with a different one in terms of shape and/or configuration of the reactant surfaces 22; 22'; 22" or in terms of quantity, nature and distribution of the binding agents A.

A person skilled in the art, in order to meet further and contingent requirements, may effect several further modifications and variations to the device, the system and the method described above, all however comprised within the scope of protection of the present invention as defined by the appended claims.

The invention claimed is:

1. A method for the ex-vivo removal of a biological and/or chemical entity (C) from an extracorporeal blood volume (B) comprising:
   a) introducing the extracorporeal blood (B) into a hollow capture chamber having a cylindrical shape, an inlet for the entry of the extracorporeal blood (B), an outlet for the outflow of the extracorporeal blood (B) and a capture element extending longitudinally within the capture chamber and movable relative to the capture chamber, the capture element:
      i) being rotatable about a longitudinal axis (a) of the capture chamber;
      ii) having a reactant surface for contacting the extracorporeal blood (B), said reactant surface comprising a plurality of binding agents (A) for the biological and/or chemical entity to be removed (C), and
      iii) a coupling and uncoupling system configured such that the capture element can be removed from the capture chamber to allow analysis of entities captured by the reactant surface, b) filtering the extracorporeal blood (B) by contact with the reactant surface having the plurality of binding agents (A) for the biological and/or chemical entity (C) to be removed; and c) extracting the extracorporeal blood (B) devoid of said biological and/or chemical entity (C) from the capture chamber;

wherein the total volume of extracorporeal blood (B) flowing inside the capture chamber is between 3 to 30 liters of blood.

2. The method according to claim 1, further comprising:

d) stopping the introduction of extracorporeal blood (B) into the capture chamber after introducing a predetermined volume of blood (B) and removing the capture element to analyze the nature and quantity of the biological and/or chemical entity (C) removed and present on the reactant surface.

3. The method according to claim 1, further comprising diagnosing and/or monitoring the progression of a tumor disease present in the extracorporeal blood wherein the extracorporeal blood is obtained from a patient suspected of having circulating tumor cell.

4. The method according to claim 1, wherein the biological and/or chemical entity to be removed (C) is a circulating tumor cell.

5. The method according to claim 1, wherein the binding agents (A) comprise one or more antibodies, or adhesion proteins, or aptamers, thereby providing the removal of epithelial, mesenchymal, hybrid epithelial-mesenchymal, and stem-like CTCs (Circulating Tumor Cells), singly and/or in clusters.

6. The method according to claim 1, wherein the reactant surface of the movable capture element is shaped like a helix.

7. The method according to claim 1, wherein the hollow capture chamber further comprises one or more conical structures having each a filtering mesh surface made of holes with a diameter equal or greater than 100 µm.

8. The method according to claim 1, wherein the plurality of binding agents (A) is distributed evenly over the entire reactant surface of the capture element.

9. The method according to claim 1, wherein the plurality of binding agents (A) consists of binding agents of a different nature, which are concentrated in specific areas of the reactant surface of the movable capture element.

10. The method according to claim 1, wherein the binding agents (A) are evenly distributed or concentrated in specific areas on an inner surface of the capture chamber.

11. The method according to claim 1, further comprising introducing an anticoagulant into the extra corporeal blood prior to the extracorporeal blood being introduced into the hollow capture chamber.

* * * * *